United States Patent [19]

Usen et al.

[11] Patent Number: 5,895,641
[45] Date of Patent: Apr. 20, 1999

[54] PROCESSES AND COMPOSITION FOR REMINERALIZATION AND PREVENTION OF DEMINERALIZATION OF DENTAL ENAMEL

[75] Inventors: Norman Usen, Marlboro; Anthony E. Winston, East Brunswick, both of N.J.

[73] Assignee: Enamelon, Cranbury, N.J.

[21] Appl. No.: 08/670,897

[22] Filed: Jun. 26, 1996

Related U.S. Application Data

[62] Division of application No. 08/465,875, Jun. 6, 1995, Pat. No. 5,605,675.

[51] Int. Cl.$^6$ .................. A61K 7/16; A61K 7/18
[52] U.S. Cl. .................. 424/52; 424/49; 424/57
[58] Field of Search .................. 424/49–88

[56] References Cited

U.S. PATENT DOCUMENTS

| | | |
|---|---|---|
| 1,698,404 | 1/1929 | Hopkins . |
| 2,605,229 | 7/1952 | Marcus .................. 252/317 |
| 2,627,493 | 2/1953 | Merckel et al. .................. 167/93 |
| 2,700,012 | 1/1955 | Merckel et al. .................. 167/93 |
| 3,679,360 | 7/1972 | Rubin . |
| 3,728,446 | 4/1973 | Roberts et al. .................. 424/49 |
| 3,747,804 | 7/1973 | Raaf et al. .................. 222/1 |
| 3,913,229 | 10/1975 | Driskell et al. .................. 32/15 |
| 3,943,267 | 3/1976 | Randol .................. 427/2 |
| 3,966,901 | 6/1976 | Cullum et al. .................. 424/52 |
| 4,048,300 | 9/1977 | Tomlinson et al. .................. 424/52 |
| 4,075,317 | 2/1978 | Mitchell et al. .................. 424/52 |
| 4,080,440 | 3/1978 | DiGiulio et al. .................. 424/49 |
| 4,083,955 | 4/1978 | Grahenstetter et al. .................. 424/49 |
| 4,097,935 | 7/1978 | Jarcho . |
| 4,108,980 | 8/1978 | Duff .................. 424/52 |
| 4,138,477 | 2/1979 | Gaffar .................. 424/52 |
| 4,141,969 | 2/1979 | Mitchell .................. 424/52 |
| 4,150,112 | 4/1979 | Wagenknecht et al. .................. 424/48 |
| 4,159,315 | 6/1979 | Wagenknecht et al. .................. 424/48 |
| 4,177,258 | 12/1979 | Gaffar et al. .................. 424/52 |
| 4,183,915 | 1/1980 | Gaffar et al. .................. 424/52 |
| 4,233,288 | 11/1980 | Cornell .................. 424/48 |
| 4,244,707 | 1/1981 | Wason .................. 51/308 |
| 4,265,877 | 5/1981 | Tenta .................. 424/48 |
| 4,280,822 | 7/1981 | Wason .................. 51/308 |
| 4,283,385 | 8/1981 | Dhabbar et al. .................. 424/52 |
| 4,340,584 | 7/1982 | Wason .................. 424/52 |
| 4,348,381 | 9/1982 | Gaffar et al. .................. 424/52 |
| 4,397,837 | 8/1983 | Raaf et al. .................. 424/51 |
| 4,405,600 | 9/1983 | Besic .................. 424/57 |
| 4,412,983 | 11/1983 | Mitchell .................. 424/52 |
| 4,415,550 | 11/1983 | Pakhomov et al. .................. 424/57 |
| 4,419,341 | 12/1983 | Kokesnik et al. .................. 424/52 |
| 4,424,203 | 1/1984 | Pakhomov et al. .................. 424/52 |
| 4,460,565 | 7/1984 | Weststrate et al. .................. 424/52 |
| 4,474,749 | 10/1984 | Kruppa .................. 424/48 |
| 4,487,757 | 12/1984 | Kiozpeoplou .................. 424/49 |
| 4,515,770 | 5/1985 | Besic .................. 424/49 |
| 4,518,430 | 5/1985 | Brown et al. .................. 106/35 |
| 4,528,180 | 7/1985 | Schaeffer .................. 424/52 |
| 4,556,561 | 12/1985 | Brown et al. .................. 424/151 |
| 4,565,691 | 1/1986 | Jackson .................. 424/52 |
| 4,603,045 | 7/1986 | Smigel .................. 424/52 |
| 4,606,912 | 8/1986 | Rudy et al. .................. 424/52 |
| 4,610,873 | 9/1986 | Rudy et al. .................. 424/52 |
| 4,612,053 | 9/1986 | Brown et al. .................. 706/35 |
| 4,672,032 | 6/1987 | Slavkin et al. .................. 435/68 |
| 4,714,608 | 12/1987 | Rolla .................. 424/52 |
| 4,812,306 | 3/1989 | Cockerell et al. .................. 424/52 |
| 4,824,681 | 4/1989 | Schobel et al. .................. 426/5 |
| 4,828,823 | 5/1989 | Li .................. 424/52 |
| 4,837,007 | 6/1989 | Duckworth et al. .................. 424/52 |
| 4,931,272 | 6/1990 | Dany et al. .................. 424/49 |
| 4,980,154 | 12/1990 | Gordon .................. 424/53 |
| 4,983,379 | 1/1991 | Schaeffer .................. 424/52 |
| 5,037,639 | 8/1991 | Tung .................. 424/57 |
| 5,041,280 | 8/1991 | Smigel .................. 424/52 |
| 5,045,305 | 9/1991 | Clarkson et al. .................. 424/52 |
| 5,047,031 | 9/1991 | Constantz .................. 606/77 |
| 5,124,160 | 6/1992 | Zibell et al. .................. 426/3 |
| 5,129,905 | 7/1992 | Constantz .................. 606/76 |
| 5,139,769 | 8/1992 | Gaffar et al. .................. 424/52 |
| 5,145,668 | 9/1992 | Chow et al. .................. 424/52 |
| 5,268,167 | 12/1993 | Tung .................. 424/52 |
| 5,378,131 | 1/1995 | Greenberg .................. 424/440 |
| 5,427,768 | 6/1995 | Tung .................. 424/52 |
| 5,437,857 | 8/1995 | Tung .................. 424/52 |
| 5,460,803 | 10/1995 | Tung .................. 424/57 |

OTHER PUBLICATIONS

International Application Publication WO94/18938, Sep. 1, 1994.

*Primary Examiner*—Shep K. Rose
*Attorney, Agent, or Firm*—Depaoli & Frenkel, P.C.

[57] ABSTRACT

The present invention relates to the problems of remineralization without demineralization of dental enamel by applying to the teeth a composition which is present in two phases which do not react with one another until introduced into the oral cavity. One phase contains at least one water-soluble calcium compound and the other contains at least one water-soluble inorganic phosphate and at least one water-soluble fluorine compound. In this way the ions which effect remineralization can be absorbed by the dental enamel and their subsequent reaction causes rehardening of demineralized areas in the dental enamel.

16 Claims, No Drawings

PROCESSES AND COMPOSITION FOR REMINERALIZATION AND PREVENTION OF DEMINERALIZATION OF DENTAL ENAMEL

This application is a division of application Ser. No. 465,875, filed Jun. 6, 1995, now U.S. Pat. No. 5,605,675.

BACKGROUND OF THE INVENTION

1. Field of the Invention

This invention relates to processes and compositions which are useful to rapidly remineralize subsurface dental enamel. More specifically, this invention relates to salt solutions, such as calcium and phosphate salt solutions, which are applied to lesions in dental enamel resulting in remineralization of subsurface dental enamel and/or mineralizing tubules in dentin thereby counteracting caries and/or hypersensitivity.

2. The Prior Art

The primary component of the enamel and dentin in teeth is calcium phosphate in the form of calcium hydroxyapatite. This material is highly insoluble at normal oral pHs. However, carious lesions form in teeth, when they are subjected to acids produced from the glycolysis of sugars by the action of various oral bacteria. This is because calcium phosphate salts are more soluble in acidic media.

Saliva is supersaturated with respect to calcium and phosphate ions. Saliva therefore helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva the addition of higher levels of dissolved calcium and phosphate ions is not easily accomplished.

Remineralization of dental enamel has been carried out experimentally both in vivo and in vitro. Some studies have concentrated on the remineralizing properties of saliva and synthetic solutions supersaturated with respect of hydroxyapatite. Such studies comprise the subject matter of U.S. Pat. Nos. 3,679,360 (Rubin) and 4,097,935 (Jarcho).

Generally, the supersaturated solutions or slurries used in these patents for remineralization experiments have been prepared from a single form of calcium phosphate. When a caries lesion is flooded with one of these supersaturated solutions, the calcium and phosphate ions in the form of precipitated hydroxyapatite remineralize the lesion.

However, these solutions are impractical for use for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solutions the pH of the solution changes. Unless the old solution is removed from contact with the tooth material, the solution may become too acidic or alkaline and damage the dental tissue.

U.S. Pat. No. 4,080,440 (Digiulio et al) discloses a metastable solution of calcium and phosphate ions at a low pH (between 2.5 to 4.0) underwhich conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258 and 4,183,915 (Gaffar et al) provide for a remineralizing solution containing supersaturated concentrations of calcium ions, phosphate ions and a fluoride source stabilized by the presence of an antinucleating agent such as diamine tetramethylenephosphonic acid. This solution is preferably adjusted to the neutral pH range where it is alleged to most effectively remineralize subsurface lesions. Even though the antinucleating agent would be expected to stabilize the solution, equilibrium of the supersaturated concentrations is still found difficult to maintain and avoid precipitation of hydroxyapatite and changes in the pH of the solution U.S. Pat. Nos. 4,083,955 (Grabenstetter et al) and 4,397,837 (Raaf et al) provide a process for remineralizing demineralized enamel by the consecutive treatment of tooth surfaces with separate solutions containing calcium ions and phosphate ions. In this process fluoride ions may be present in the phosphate solutions. It is immaterial which ionic solution is used to treat the teeth first. By sequentially applying calcium and phosphate ions to the tooth surface high concentrations of the ions are able to penetrate into lesions in solution form, where they precipitate as a calcium phosphate salt when ions from the second treatment solution diffuse in. While apparently successful this method involves the inconvenience of a plurality of sequential applications which can also be found to be time consuming.

Another problem with known remineralization techniques is that the remineralization may stop before the lesion is completely remineralized due to build up of the remineralized tooth material in or on the outer layer of the tooth's surface. This build up occurs when the rate of remineralization is too fast and prevents the diffusion of the mineral into the deeper regions of the lesion, thus thwarting the full remineralization of the tooth.

There is a need for a method of remineralizing dental enamel that does not require excessive amounts of solution and inordinately long or frequent exposure times.

It is the object of the present invention to provide a process and especially a composition for the remineralization and the prevention of demineralization of human teeth, which process and composition are capable of effectively incorporating calcium ions, phosphate ions and fluoride ions into the dental enamel, the composition also being easily usable by the consumer and not differing significantly, in flavor and appearance, from customary dental cosmetics.

SUMMARY OF THE INVENTION

In accordance with the present invention the problems of remineralization, without demineralization are solved by applying to the teeth a composition which is present in two phases which do not react with one another until introduced into the oral cavity. One phase contains at least one water-soluble calcium compound and the other contains at least one water-soluble inorganic phosphate and at least one water-soluble fluorine compound. In this way the ions which effect remineralization can be absorbed by the dental enamel and their subsequent reaction causes rehardening of demineralized areas in the dental enamel.

It has been found that effective remineralizing treatments can be prepared by directly combining solutions or preparations with soluble salts containing high concentrations of calcium, phosphate and fluoride ions and applying them to teeth at moderate pHs. However, the calcium must be prevented from the reaction with the phosphate ions or fluoride ions until immediately before use. This can be accomplished by providing a dual container or tube system in which the calcium ions are in a different container or tube than the phosphate or fluoride ions or by incorporating undissolved soluble salts containing these ions into a single base in which the ions are separated physically, e.g., by the encapsulation of at least one or are insoluble in said base.

For two part systems, two part toothpastes, gels, professional gels, i.e., those which are applied professionally or are obtained by a prescription, mouthwashes, and the like are prepared, wherein part I contains from about 0.05% to about 15% water-soluble calcium salt, and part II contains from about 0.05% to 15% water-soluble phosphate salt and from about 0.01% to 5% fluoride releasing agent such that when the two parts are mixed the pH is between about 4.5 and 10.0, and preferrably between about 5.5 and 7.0. The two parts are mixed and immediately applied to the teeth being treated. It has been found that such combinations produce rapid remineralization of lesions and are much more effective than conventional fluoride containing toothpastes in remineralizing teeth.

The compositions of the invention give substantially improved remineralization and prevention of demineralization of human teeth as compared with prior art compositions.

The disadvantages of the prior art methods are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Further, the present invention may be conveniently practiced by the public without substantially changing their dental care habits.

DESCRIPTION OF THE INVENTION

The present invention lies in the discovery that dental enamel may be remineralized by the application of certain soluble salts yielding ions which will react to form a desirable remineralizing precipitate. The application consists of the simultaneous use of a two part system wherein the first part is a reactant paste, gel or solution of a soluble salt which is placed in contact with the tooth surface. In this first reactant part are selected cations with diffuse through the tooth surface to its demineralized subsurface. In the second part a reactant paste, gel or solution containing selected anions is placed simultaneously in contact with the tooth surface. The anions diffuse through the tooth surface to the demineralized subsurface with the cations and form a precipitate which is bound to the tooth structure. As a results the tooth's subsurface is remineralized when an effective amount of the two part system is utilized.

By "effective amount of remineralizing system or agent" is meant an amount when used in accordance with this invention will bring about the remineralizing of teeth having caries lesions, or the mineralizing of normal teeth to prevent caries from forming by utilizing a toothpaste, gel, or mouthwash having the various components in the amounts set forth below.

Concentrations of the soluble salt are from about 0.05 to 15% or the limit of solubility of the salt. Excess salt can be presents if desired. Concentrations from about 0.10% to 10% are preferred. The concentrations of the soluble salts containing the desired anions are essentially the same as those for the water-soluble salts containing the desired cations.

Although many precipitates are within the broad scope of this invention, by depositing a precipitate less soluble than the original enamel, the remineralized subsurface can be made to be more resistant to demineralization than was the original enamel. Due to the presence of a fluoride ion, the remineralized enamel is more resistant to demineralization than was the original enamel. The concentration of salt containing fluoride ion in the solution may be from about 0.01% to 5.0%, but from about 0.02% to 2.0% is preferred.

In order to effect remineralization of the dental enamel, an effective amount of the desired cations and anions must be employed in the oral cavity. The amount of solution placed in the mouth must contain at least 100 ppm of desired cations and 250 ppm of desired anions and preferably contains more than 3,000 ppm of desired cations and 3,000 ppm of desired anions. It is preferred to provide a level of fluoride ions between about 20 ppm to 5,000 ppm in the oral cavity from the dentifrice or professionally applied or prescribed gel.

While the length of time of contact between the dissolved salts and the tooth's surface is not critical, it is necessary for the length of time to be great enough to allow diffusion of the ions through the tooth's surface to the demineralized subsurface. It is submitted that at least ten seconds is required for this diffusion and preferably it should be greater than thirty seconds.

Each solution should have a pH of from about 4.5 to 10.0 and preferably between about 5.5 and 7.0 before and after the precipitation reaction, and be otherwise compatible in the oral environment. While some precipitation may occur, not all of the ions should combine prematurely in the solution to form a precipitate, but must be able to diffuse through the surface of the tooth to a demineralized subsurface area and be able to form an insoluble salt with ions of the other solution.

The solutions and the insoluble precipitates must have acceptable levels of toxicity (i e., the particular ions, in the amounts used in the remineralization process, must be non-toxic).

In the preferred embodiment of the present inventions the remineralizing cationic solution contains about 0.05% to 15%, preferably about 0.10% to 10% of a dissolved calcium salt yielding calcium ions. The remineralizing anionic solution contains from about 0.05% to 15%, preferably about 0.10% to 10%, of dissolved phosphate salt yielding phosphate ions and from about 0.01% to 5.0%, preferably from about 0.02% to 2.0%, of a soluble fluoride salt yielding fluoride ions.

The resulting precipitate is a calcium phosphate or hydroxyapatite, the natural constituent of tooth enamel, with incorporated fluoride ions. Not only does this process result in remineralized enamel, but the remineralized enamel may be more resistant to subsequent demineralization than was the original enamel.

As the calcium compound it is, in principle, possible to employ, in the preparations of the invention, all water-soluble toxicologically harmless calcium compounds. A compound is considered to be water-soluble when at least 0.25 gram thereof dissolves in 100 ml of $H_2O$ at 20° C.

Suitable water-soluble calcium compounds are, for example, calcium chlorides calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate or mixtures of water-soluble calcium compounds. Calcium nitrate is preferred. In the compositions of the invention for the remineralization of human dental enamel, at least about 100 ppm of calcium ions should be present; the upper limit is about 35,000 ppm of calcium ions.

Suitable water-soluble inorganic phosphates within the scope of the present invention are, for example, monobasic-calcium phosphate, dipotassium phosphate, sodium metaphosphate, monosodium phosphate and the alkali salts and ammonium salts of orthophosphoric acid, such as potassium, sodium or ammonium orthophosphate. monobasic-calcium phosphate and dipotassium phosphate are preferred. The concentration of the phosphate ions is preferably about 250 to 40,000 ppm; solubility in water is defined as in the case of the calcium compounds.

If desired, water-soluble salts yielding both calcium and phosphate ions, such as monobasic-calcium orthophosphate, may be employed. The compositions of the invention for the remineralization or prevention of demineralization of human teeth also contain water-soluble fluoride compounds, the caries-prophylactic activity of which has for a long time been considered to be established. These compounds are preferably present in the phase containing phosphate in order to avoid the formation of sparingly soluble calcium fluoride.

Suitable fluoride compounds are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites.

Organic fluorides, such as the known amine fluorides are also suitable for use in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition other water-soluble monofluorophosphate salts may be employed including ammonium monofluorophosphate aluminum monofluorophosphate, and the like. If monofluorophosphate salts are used as the fluoride source, they could be present in the first component along with the calcium cations without departing from the present invention. However, this is less desirable due to the potential loss of fluoride.

Suitable toothpastes and gels can be made by employing in both the anionic and cationic portions of the toothpaste, from about 0.5% to 50%, preferably from about 5% to 25%, of an abrasive, from about 0.2% to 5% of a sudsing agent, from about 0.1% to 5% of a binding agent, from 0% to 50% of a humectant, and the balance, water and minors.

The pH of a component part of the toothpaste or gel containing the active cationic ingredients preferably has a pH of more than about 3. The mixture of the two portions which is placed in the mouth, however, must have a pH of from about 4.5 to about 10.0 and, preferably, between about 5.5 and 7.0. The pH's of the cationic portion and the anionic portion can be adjusted so long as the above parameters are not exceeded.

Suitable abrasives include silica xerogels. Other conventional toothpaste abrasives can be used in the compositions of this invention, and include beta-phase calcium pyrophosphate, dicalcium phosphate dihydrate, anhydrous calcium phosphate, calcium carbonate, zironium silicate, and thermosetting polymerized resins. Silica aerogels and the insoluble metaphosphates such as insoluble sodium metaphosphate can be used. Mixtures of abrasives can be also be used. Silica xerogel abrasives are preferred.

Suitable sudsing agents are those which are reasonably stable and form suds throughout the period of application. Preferably, non-soap anionic or nonionic organic synthetic detergents are employed. Examples of such agents are water-soluble salts of alkyl sulfate having from 10 to 18 carbon atoms in the alkyl radical, such as sodium lauryl sulfates water-soluble salts of sulfonated monoglycerides of fatty acids having from 10 to 18 carbon atoms, such as sodium monoglyceride sulfonate, salts of $C_{10}$–$C_{18}$ fatty acid amides of taurine, such as sodium N-methyl taurate, salts of $C_{10}$–$C_{18}$ fatty acid esters of isethionic acids and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material is added to thicken and provide a desirable consistency for the present compositions. Suitable thickening agents are water-soluble salts of cellulose ethers, such as sodium carboxymethyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum.

It is also desirable to include some humectant material in a toothpaste or gel to keep it from hardening. Suitable humectants include glycerine, sorbitol, polyethylene glycol, propylene glycol, and other edible polyhydric alcohols as well as mixtures thereof.

Toothpaste or gel compositions may also contain flavoring agents such as oil of wintergreen, oil of peppermint, oil of spearmint, oil of sassafras, and oil of clove. Toothpaste or gel compositions may also contain sweetening agents such as saccharin, dextrose, levulose, sodium cyclamate, and aspartame Mixtures of sugar with a sweetner, e.g., sucralose, are contemplated.

It is, of course, also possible to manufacture one or both phases in the form of a transparent gel, the gel-forming agents to be used including known thickeners, for example the alkali salts of polyacrylic acid, and also preferentially dehydrated silicon dioxide gels of particle size about 2 to 20 microns and specific surface area about 200 to 900 m$^2$/g.

The remineralizing systems herein can also be provided in the form of a mouthwash product. Both the cationic and anionic parts of mouthwashes can be made in accordance with the following. Mouthwashes generally comprise an aqueous solution of ethyl alcohol and flavoring materials. The alcohol provides an antibacterial effect, solubilizes the flavoring materials and provides a pleasant mouth feeling. Alcohol-free mouthwashes are now, however, gaining in popularity. Optionally, mouthwashes also contain additional antibacterial agents and humectants such as glycerine and sorbitol which give a moist feeling to the mouth.

Typically, mouthwashes contain about 0 to 30%, preferably about 0 to 20%, ethyl alcohol; about 30% to 90% water; about 0 to 20% glycerine or other humectant; about 0 to 0.1% of an antibacterial agent; about 0 to 0.2% of a soluble fluoride source, about 0.01% to 0.5% of a sweetening agents about 0.01% to 2.0% of a flavoring agent, and from about 0.1% to 1% of an emulsifier-surfactant.

Examples of suitable flavoring agents include heliotropyl nitrile, wintergreen oil (methyl salicylate), oil of peppermint, oil of assia, oil of anise, oil of cinnamon, and mixtures thereof. Suitable sweetening agents include saccharin, glycerine, sorbitol, levulose, and 6-(tribluoromethyl)-tryptophane and aspartyl phenylalanine methyl ester.

In one embodiment of this invention there is provided a product for remineralizing dental enamel comprising: (i) a first component comprising from about 0.05% to 15.0%, preferably about 0.10% to 10%, water-soluble calcium salt; (ii) a second component comprising from about 0.05% to 15.0%, preferably about 0.10% to 10% water-soluble phosphate salt together with from about 0.01% to 10.0% and preferably from about 0.02% to 5.0% fluoride releasing agent, (iii) a dispensing container comprising at least two discreet compartments each with an outlet end, the first compartment storing the first component which includes soluble calcium salt and the second compartment storing the second component which includes soluble phosphate salt together with the fluoride source, (iv) a closure mechanism for closing the compartments; and (v) wherein when the two components are mixed the pH in between about 4.5 and 10.0 and preferably between about 5.5 and 7.0.

A plurality of packaging methods may be employed in order to separately contain or store the two components and provide effective dispensing thereof into the oral cavity.

Thus, the two components of a toothpaste, gel, cream, or the like, may be simultaneously dispensed from separate collapsible tubes preferably made of plastic, a plastic and metal laminate, etc. For convenience and in order to aid in dispensing substantially equal amounts of the components, the tubes may be held together by banding or cementing, preferably along the corresponding ventral sides of the tubes.

In another embodiment the two tubes may be constructed to have abutting, preferably flats sidewall portions. In the forgoing embodiments the mouths of the tubes are usually sufficiently close so that sufficient quantities of the components of the toothpaste or gel may be simultaneously dispensed directly on the toothbrush with the tubes the being capped separately.

Alternatively, another packaging method comprises loading each component of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and aniomic components, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of outer tube and the mouth of the inner tube. The closures of this tube-within-a-tube, (which can screw on the outer tube or simply be held by pressure), may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement comprises of a pressurized container which is provided with two compartments and two spouts. The internal pressure of the compartments is maintained by a pressurized gas, i e., nitrogen, at the bottom of each compartment. Operation of a mechanical actuator actuates valves which release the contents of the compartments through the spouts causing discharge of the paste or gel components onto a brush. The mouthwash or rinse and similar liquid embodiments are maintained in a manner similar to the pastes or gels in that during storage, each of the components are maintained separate from one another to prevent premature reactions. Upon dispensing, the components mix and react in the oral cavity to effect remineralization of dental enamel. The liquid components can therefore be stored each in separate compartments of a dual-compartment dispenser. The dispenser usually includes a closure system comprising for example, an inclined crown portion, at least two pouring spouts extending upwardly from an upper surface of the crown portion and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve as a window function for gauging the amounts of liquid remaining in the dispenser. The walls of the containers can be scribed or otherwise calibrated to assist in dispensing the correct remineralizing amount of product.

While applicants do not wish the scope of the present invention to be limited by theory, it is believed that the calcium, phosphate, and fluoride ions diffuse through the tooth surface to the demineralized subsurface and precipitate in the demineralized subsurface where they remineralize the tooth structure. This is surprising because sufficient calcium, phosphate, and fluoride ions remain soluble for a period of time sufficient to permit their diffusion into the demineralized subsurface of the dental enamel. This is accomplished by combining the particular ions just prior to their application to the tooth in a solution having a pH of about 4.5 to 10 and preferably from about 5.5 to 7 at which pH enough of the calcium, phosphate, and fluoride ions remain soluble for the period of time required to remineralize the lesions of the dental enamel. As hereinbefore described, the calcium and phosphate ions are stored separately to avoid the premature precipitation of calcium phosphate.

Chemically equivalent concentrations of the first and second solutions are not necessary as long as the molar ratio of calcium and phosphate ions in the mixture is from about 0.01 to up to 100 to 1. It is preferred that the ratio is from about 0.2 to 1 up to 5 to 1, and it is most preferred that the ratio is about 1.67 to 1, the ratio of calcium to phosphate in natural tooth enamel (hydroxyapatite).

While completely aqueous solutions are preferred in the present inventions non-aqueous solvents may be employed in combination with water. For example, suitable nonaqueous solvents include ethyl alcohol, glycerine and propylene glycol. Solvent systems suitable for use in the present invention are those which are capable of dissolving the salts employed in the invention and which are safe for use in the mouth.

With regard to the period of time of exposure of the solutions to the teeth, it is necessary that the length of time be great enough to allow diffusion of the ions into the demineralized subsurface. At least about ten seconds are required for this diffusion. The solution is preferably applied to the teeth for from about 10 seconds to about 5 minutes.

The pH of the solution remains relatively constant after its introduction into the oral cavity. Calcium phosphate readily precipitates at this pH, but most surprisingly while some of the precipitation may occur immediately and some small amount even before application to the teeth, sufficient calcium, phosphate and fluoride ions remain in solution to diffuse into the teeth and remineralize the demineralized dental enamel. It is believed that the ability of the solutions to provide ions for remineralization is greatest upon their first introduction into the oral cavity, thereafter decreasing.

The time period between the mixing of the first and second solutions and the application of the mixture to the teeth should not exceed 1 minute, and preferably is less than 1 minute. With a toothpaste, gel, and the like, mixing is achieved on the surface to the teeth while brushing. The essence of the present invention lies in the mixing of components and the quick and timely application of the resulting solution which will precipitate calcium phosphate, calcium fluoride, and calcium fluoro-apatite in the subsurface enamel of the teeth. Before such precipitation occurs, the mixture comprising the solution must quickly be applied to the teeth. Surprisingly, the solution can have a pH of about 4.5 to 10, but preferably about 5.5 to 7 to achieve this result. At a pH below about 3, demineralization occurs rapidly. A pH below 2.5 is generally undesirable from a safety standpoint.

The pH of the solutions of the present invention may be adjusted to the pH desired by methods well known in the art. The pH may be lowered by the addition of any acid which is safe for use in the oral cavity and which yields the desired pH at the amount employed. Examples of suitable acids are acetic acid, phosphoric acid, hydrochloric acid, citric acid and malic acid.

The following Examples illustrate the invention: In the Examples and elsewhere herein parts and percent are by weight unless otherwise stated.

EXAMPLE 1

Artificial lesions, about 50 u deep, were formed in one surface of bovine enamel chips using a demineralizing Carbopol gel, which was used to treat the specimens for 72 hours. The surface hardness of the surface to be treated was then measured.

The regimen cycle consisted of a 30 minute demineralization in a standard demineralizing solution followed by a 5 minute treatment of the test products diluted 1 part product to two parts human saliva, followed by a 60 minute remineralization in human saliva. Overnight, which was every fifth cycle, the specimens were kept with a layer of saliva and stored in a cold room. The test ran for three days, from a total of 15 demineralization:treatment:remineralization cycles.

For the treatment cycle, the two parts of the remineralizing test agents of the example were separately diluted 1 part product to 2 parts saliva and mixed together immediately before immersion of the enamel specimens.

The two part oral remineralizing treatment was prepared as follows:

|  | Part A | Part B |
|---|---|---|
| Water | 71 | 66.45 |
| Calcium nitrate | 4 | 0.00 |
| Dipotassium phosphate |  | 8.00 |
| Sodium fluoride |  | 0.55 |
| Glycerin | 25 | 25.00 |

|  | Part A | Part B |
|---|---|---|
| Acetic acid | To adjust pH of A & B mixture of 5.5 immediately after mixing. | |

Hardness Increase Due to Treatment (Vickers Hardness Units)

|  | Example 1 | Crest | 1200 ppm Fluoride at pH 5.5 | Placebo |
|---|---|---|---|---|
| 5 cycles | 17.0 + 1.9 | 11.8 + 1.4 | | |
| 10 cycles | 23.6 + 1.4 | 13.0 + 3.6 | 13.7 + 2.3 | 3.9 + 0.7 |
| 15 cycles | 34.8 + 2.8 | 11.2 + 1.7 | | |
| 20 cycles | 48.2 + 2.8 | 17.5 + 2.2 | | |

Fluoride Increase Due to Treatment ($ug/cm^3$)

|  | Example 1 | Crest | 1200 ppm Fluoride at pH 5.5 | Placebo |
|---|---|---|---|---|
| 5 cycles | 2433 | 1879 | | |
| 10 cycles | 3523 | 2082 | 2928 | 244 |
| 15 cycles | 4431 | 2196 | | |
| 20 cycles | 4749 | 2964 | | |

The results show much greater remineralization, as measured by hardness increase and fluoride uptake, due to treatment with the product of Example 1 than Crest, fluoride solution or placebo.

EXAMPLES 2, 3, and 4

Two part oral remineralizing treatments were prepared as follows:

|  | Example 2 | | Example 3 | | Example 4 | |
|---|---|---|---|---|---|---|
|  | A | B | A | B | A | B |
| Water | 73 | 66.45 | 74 | 66.45 | 73 | 66.45 |
| Calcium nitrate | 2 | 0.00 | 1 | 0.00 | 2 | 0.00 |
| Dipotassium phosphate | | 8.00 | | 8.00 | | 8.00 |
| Sodium fluoride | | 0.55 | | 0.55 | | 0.55 |
| Glycerin | 25 | 25.00 | 25 | 25.00 | 25 | 25.00 |
| Acetic acid | To adjust pH of A & B mixture to 5.5 immediately after mixing. | | To adjust pH of A & B mixture to 5.5 immediately after mixing. | | To adjust the pH of A & B mixture to 4.5 immediately after mixing. | |

The same cyclic regimen used to evaluate Example 1 was used to evaluate the remineralizing efficacy of the above formulations compared with Crest. In this study 15 cycles were used.

Hardness and Fluoride Increase Due to Treatment

|  | Example 2 | Example 3 | Example 4 | Crest |
|---|---|---|---|---|
| Hardness increase | 45.1 + 2.9 | 37.6 + 2.4 | 32.7 + 2.5 | 14.2 + 1.8 |
| Fluoride uptake | 4677 + 219 | 5686 + 138 | 4495 + 343 | 2099 + 182 |

The results show much greater remineralization, as measured by hardness increase and fluoride uptake, due to treatment with Examples 2, 3, and 4 of the invention than Crest.

EXAMPLES 5, 6, 7, 8, 9 and 10

Two part oral remineralizing treatments were prepared as follows:

|  | Example 5 | | Example 6 | | Example 7 | | Example 8 | | Example 9 | | Example 10 | |
|---|---|---|---|---|---|---|---|---|---|---|---|---|
|  | A | B | A | B | A | B | A | B | A | B | A | B |
| Water | 71.2 | 70.45 | 67.4 | 66.86 | 67.4 | 66.45 | 63.6 | 62.45 | 67.4 | 66.45 | 67.4 | 66.45 |
| Calcium nitrate | 3.8 | 0.00 | 7.6 | 0.00 | 7.6 | 0.00 | 11.4 | 0.00 | 11.4 | 0.00 | 7.6 | 0.00 |
| Dipotassium phosphate |  | 4.00 |  | 8.00 |  | 8.00 |  | 12.00 |  | 8.00 |  | 8.00 |
| Sodium fluoride |  | 0.55 |  | 0.14 |  | 0.55 |  | 0.55 |  | 0.55 |  | 0.55 |
| Glycerin | 25.0 | 25.00 | 25.0 | 25.00 | 25.0 | 25.00 | 25.0 | 25.00 | 25.0 | 25.00 | 25.0 | 25.00 |
| Acetic acid | To adjust pH of A & B mixture to 5.5 immediately after mixing. | | To adjust pH of A & B mixture to 5.5 immediately after mixing. | | To adjust the pH of A & B mixture to 4.5 immediately after mixing. | | To adjust pH of A & B mixture to 5.5 immediately after mixing. | | To adjust pH of A & B mixture to 5.5 immediately after mixing. | | To adjust the pH of A & B mixture to 4.5 immediately after mixing. | |

The same cyclic regimen used to evaluate Examples 1–4 was used to evaluate the remineralizing efficacy of the Examples 5–10 compared with Crest. In this study 15 cycles were used.

Hardness Increase Due to Treatment

Vickers Hardness Units

|  | Hardness increase |
|---|---|
| Example 5 | 97 + 6 |
| Example 6 | 97 + 6 |
| Example 7 | 95 + 2 |
| Example 8 | 84 + 5 |
| Example 9 | 83 + 5 |
| Example 10 | 82 + 3 |
| Crest | 20 + 2 |

The results show much greater remineralization, as measured by hardness increases due to treatment with Examples 5–10 of the invention than Crest. Example 6 shows that even when the fluoride concentration is lowered to supply only 27 percent of that supplied by Crest (i.e. 275 ppm versus 1150 ppm) much higher levels of remineralization are still achieved.

Examples 11–16 illustrate various embodiments remineralizing toothpaste formulations of the invention as follows:

|  | Example 11 | | Example 12 | | Example 13 | |
|---|---|---|---|---|---|---|
|  | A | B | A | B | A | B |
| Glycerin | 10.0 | 10.0 | 5.0 | 4.0 | 6.0 | 6.0 |
| Sorbitol | 40.0 | 40.0 | 30.0 | 30.0 | 34.0 | 30.0 |
| Water | 18.5 | 19.32 | 17.9 | 14.82 | 32.3 | 29.5 |
| Silica abrasive | 15.0 | 15.0 | 0.0 | 0.0 | 10.0 | 5.0 |
| Silica thickener | 8.0 | 8.0 | 0.0 | 0.0 | 8.0 | 5.0 |
| DCPDH | 0.0 | 0.0 | 40.0 | 0.0 | 0.0 | 0.0 |
| Calcium nitrate | 5.0 | 0.0 | 3.5 | 0.0 | 6.0 | 0.0 |
| Monosodium phosphate | 0.0 | 3.7 | 0.0 | 6.5 | 0.0 | 10.0 |
| Sodium meta-phosphate | 0.0 | 0.0 | 0.0 | 40.0 | 0.0 | 10.0 |
| CMC | 1.0 | 1.0 | 1.2 | 1.5 | 1.4 | 1.5 |
| Sodium Lauryl sulfate | 1.5 | 1.5 | 1.2 | 1.8 | 1.3 | 1.5 |
| Sodium fluoride | 0.0 | 0.48 | 0.0 | 0.48 | 0.0 | 0.1 |
| Flavor | 0.8 | 0.8 | 0.9 | 0.7 | 0.7 | 1.0 |
| Saccharin | 0.2 | 0.2 | 0.3 | 0.2 | 0.3 | 0.4 |

|  | Example 14 | | Example 15 | | Example 16 | |
|---|---|---|---|---|---|---|
|  | A | B | A | B | A | B |
| Glycerin | 10.0 | 10.0 | 5.0 | 4.0 | 6.0 | 6.0 |
| Sorbitol | 40.0 | 40.0 | 30.0 | 30.0 | 34.0 | 30.0 |
| Water | 18.5 | 19.32 | 17.9 | 14.82 | 32.3 | 29.5 |
| Silica abrasive | 15.0 | 15.0 | 0.0 | 0.0 | 10.0 | 5.0 |
| Silica thickener | 8.0 | 8.0 | 0.0 | 0.0 | 8.0 | 5.0 |
| DCPDH | 0.0 | 0.0 | 40.0 | 0.0 | 0.0 | 0.0 |
| Calcium nitrate | 5.0 | 0.0 | 3.5 | 0.0 | 6.0 | 0.0 |
| Monosodium phosphate | 0.0 | 3.7 | 0.0 | 6.5 | 0.0 | 10.0 |
| Sodium meta-phosphate | 0.0 | 0.0 | 1.2 | 1.5 | 1.4 | 1.5 |
| Sodium Lauryl sulfate | 1.5 | 1.5 | 1.2 | 1.8 | 1.3 | 1.5 |
| Sodium fluoride | 0.0 | 1.81 | 0.0 | 0.0 | 0.0 | 0.0 |
| Sodium MFP | 0.0 | 0.0 | 0.0 | 1.52 | 0.0 | 0.2 |
| Flavor | 0.8 | 0.8 | 0.9 | 0.7 | 0.7 | 1.0 |
| Saccharin | 0.2 | 0.2 | 0.3 | 0.2 | 0.3 | 0.4 |

Example 17 illustrates an embodiment of a remineralizing Mouthwash formulation as follows:

| | EXAMPLE 17 | |
|---|---|---|
|  | Part A | Part B |
| Glycerin | 10.000 | 10.0 |
| Ethanol | 20.000 | 20.0 |
| Sodium fluoride | 0.055 | 0.00 |
| Calcium nitrate | 0.000 | 5.00 |
| Dipotassium phosphate | 5.000 | 0.00 |
| Monopotassiumphosphate | 0.000 | 0.00 |
| Water | QS | QS |

What is claimed is:

1. A method for remineralizing at least one lesion formed in a subsurface of at least one tooth and/or mineralizing at least one exposed dentinal tubule in said subsurface of said tooth, consisting essentially of:
   (i) dispensing a first discrete component consisting essentially of from about 0.05% to 15.0% of at least one water-soluble calcium salt, wherein the calcium salt is calcium chloride or calcium nitrate;
   (ii) dispensing a second discrete component consisting essentially of from about 0.05% to 15.0% of at least one water-soluble phosphate salt and from about 0.01% to 5.0% of at least one water-soluble fluoride salt, wherein the first and second components each have a pH in water such that a mixed aqueous solution formed by mixing the first and second components with water and/or saliva has a pH of from 4.5 to 10.0;
   (iii) mixing said first discrete component and said second discrete component with water and/or saliva to form a mixed aqueous solution having a pH of from 4.5 to 10 and consisting essentially of calcium ions released by the calcium salt, phosphate ions released by the phosphate salt and fluoride ions released by the fluoride salt; and
   (iv) immediately after step (iii), applying said mixed aqueous solution to the at least one tooth for a sufficient time that the calcium and phosphate ions diffuse into the subsurface of said tooth and subsequently precipitate to form hydroxyapatite, thereby remineralizing the at least one lesion and/or mineralizing the at least one exposed dentinal tubule.

2. The method according to claim 1 wherein said first and second components are a paste, a gel, or a professional gel and are extruded together onto a toothbrush.

3. The method according to claim 1 wherein the brushing takes place within about one minute after extruding said components and placing them onto the toothbrush.

4. The method according to claim 1 wherein the period of application of calcium and phosphate ions to the teeth is from about 10 seconds up to 5 minutes.

5. The method according to claim 1 wherein the first component is comprised of from about 0.10% to 10.0% of said calcium salt.

6. The method according to claim 1 wherein the second component is comprised of from about 0.10% to 10.0% of said phosphate salt.

7. The method according to claim 1 wherein the second component contains from about 0.02% to 2.0% of said water-soluble fluoride salt.

8. The method according to claim 1 wherein the resulting mixture has a pH of from about 5.5 to 7.0.

9. The method according to claim 1 wherein the molar ratio of calcium and phosphate ions in the two components is from about 0.01 to 1 up to 100.0 to 1.

10. The method according to claim 1 wherein the molar ratio of calcium and phosphate ions in the two components is from about 0.2 to 1 up to 5.0 to 1.

11. The method according to claim 1 wherein the first component contains from about 100 ppm to 35,000 ppm calcium ions, and the second component contains from about 250 ppm to 40,000 ppm phosphate ions and from about 20 ppm to 5,000 ppm fluoride ions.

12. The method according to claim 1, wherein the phosphate salt is selected from the group consisting of dipotassium phosphate, sodium metaphosphate, and monosodium phosphate.

13. The method according to claim 1, wherein the phosphate salt is selected from the group consisting of alkali metal salts of orthophosphoric acid and ammonium salts of orthophosphoric acid.

14. The method according to claim 13, wherein the phosphate salt is selected from the group consisting of potassium orthophosphate, sodium orthophosphate, and ammonium orthophosphate.

15. A method for remineralizing at least one lesion formed in a subsurface of at least one tooth and/or mineralizing at least one exposed dentinal tubule in said subsurface of said tooth, comprising the steps of:
   (1) providing a two-component product consisting essentially of:
      (a) a first discrete component consisting essentially of from about 0.05% to 15.0% by weight of at least one water-soluble calcium salt; and
      (b) a second discrete component consisting essentially of from about 0.05% to 15.0% by weight of at least one water-soluble phosphate salt and from about 0.01% to 5.0% by weight of at least one water-soluble fluoride salt, wherein the first and second discrete components each have a pH in water such that a mixed aqueous solution formed by mixing said first and second components with water and/or saliva has a pH of from 4.5 to 10.0, further wherein the first and second discrete components are simultaneously released from said product when said product is mixed with water and/or saliva;
   (2) mixing said product with water and/or saliva so as to cause the first and second discrete components to be simultaneously released from the product into the water and/or saliva, thereby forming a mixed aqueous solution having a pH of from 4.5 to 10.0 and consisting essentially of calcium ions released by the calcium salt, phosphate ions released by the phosphate salt and fluoride ions released by the fluoride salt; and
   (3) immediately after step (2), applying the mixed aqueous solution to a surface of said at least one tooth, whereby an amount of said calcium ions, an amount of said phosphate ions and an amount of said fluoride ions diffuse through the surface of said tooth to the subsurface of said tooth, where the diffused calcium ions, diffused phosphate ions and the diffused fluoride ions react together to form an insoluble precipitate on said lesion and/or said exposed dentinal tubule, thereby remineralizing said lesion and/or mineralizing said exposed dentinal tubule.

16. The method according to claim 15, wherein said calcium salt is calcium chloride or calcium nitrate.

* * * * *